(12) United States Patent
Kim et al.

(10) Patent No.: US 6,383,451 B1
(45) Date of Patent: May 7, 2002

(54) ELECTRIC RESISTANCE SENSOR FOR MEASURING CORROSION RATE

(75) Inventors: Young-Geun Kim, Ansan; Seng-Min Lee, Seoul; Young-Tai Kho, Ansan; Hong-Seok Song, Seoul; Deok-Soo Won, Ansan, all of (KR)

(73) Assignee: Korea Gas Corporation, Kyungki-Do (KR)

( * ) Notice: Subject to any disclaimer, the term of this patent is extended or adjusted under 35 U.S.C. 154(b) by 0 days.

(21) Appl. No.: 09/393,204

(22) Filed: Sep. 9, 1999

(51) Int. Cl.[7] .............................................. G01N 17/00
(52) U.S. Cl. ...................... 422/53; 73/335.05; 436/149; 324/71.1
(58) Field of Search ............................ 422/53; 205/118, 205/775.5; 204/404; 324/700, 71.1; 436/6; 166/250.05; 376/159

(56) References Cited

U.S. PATENT DOCUMENTS

| | | | | |
|---|---|---|---|---|
| 4,179,653 A | * | 12/1979 | Davies et al. ............... | 324/700 |
| 4,454,006 A | * | 6/1984 | Hausler et al. .............. | 205/776 |
| 4,780,664 A | * | 10/1988 | Ansuini et al. .............. | 324/700 |
| 5,286,357 A | * | 2/1994 | Smart et al. ................. | 205/776 |
| 5,310,470 A | * | 5/1994 | Agarwala et al. ............ | 204/404 |
| 5,473,643 A | * | 12/1995 | Hohorst ....................... | 376/159 |
| 5,712,559 A | * | 1/1998 | Moore et al. ............... | 324/71.1 |
| 5,896,034 A | * | 4/1999 | Marshall ...................... | 324/700 |
| 5,977,782 A | * | 11/1999 | Kordecki ..................... | 324/700 |
| 6,015,484 A | * | 1/2000 | Martinchek et al. ...... | 205/775.5 |
| 6,025,199 A | * | 2/2000 | Kokemullet et al. ........... | 436/6 |
| 6,131,659 A | * | 10/2000 | Johnson .................. | 166/250.05 |
| 6,264,824 B1 | * | 7/2001 | Reid et al. ................ | 205/775.5 |

* cited by examiner

*Primary Examiner*—Jill Warden
*Assistant Examiner*—Brian J. Sines
(74) *Attorney, Agent, or Firm*—Greenberg Traurig, LLP; Eugene C. Rzucidlo

(57) ABSTRACT

The present invention relates to an electric resistance sensor for measuring a corrosion rate, and in particular to an electric resistance sensor for measuring a corrosion rate which can measure a slight corrosion resulting from pitting by using a plurality of conductive thin lines, a fabrication method therefor and a measurement method using the same.

8 Claims, 5 Drawing Sheets

ELECTRIC RESISTANCE SENSOR FOR MEASURING CORROSION RATE

BACKGROUND OF THE INVENTION

1. Field of the Invention

The present invention relates to an electric resistance sensor for measuring a corrosion rate, and in particular to an electric resistance sensor for measuring a corrosion rate not only when the primary type of corrosion is pitting but also when the corrosion rate is too late to accurately measure utilizing conventional sensors by using a plurality of conductive thin lines, a fabrication method therefor and a measurement method using the same.

2. Description of the Background Art

As a method for measuring a corrosion rate, there has been widely used method of measuring the variation in electric resistance. In this method, the resistance probes have been fabricated from materials of interest in a plate of wire shape.

In accordance with the conventional method for measuring the corrosion rate, the measuring probe is quite thick because it is mechanically processed. Therefore, a resistance variation of the probe, as a result of corrosion, is small in regard to a slight corrosion. This means that the conventional probes can not be utilized to measure the corrosion rate in cases when the corrosion rate is small. In other words, one can measure the corrosion rate only when the rate is high enough to result in a significant thickness reduction.

Consequently, there is a demand for a technique of measuring a precise corrosion rate even in an environment where the rate of corrosion is low, in order to achieve stability, precision and accuracy in maintenance and management of the facilities. The core of this demanding technology is a development of sensors having improved sensitivity and accuracy. Film-type sensors enable one to measure and monitor a slight change in corrosion behavior which can not be detected utilizing conventional plate or wire type sensors.

SUMMARY OF THE INVENTION

Accordingly, it is a primary object of the present invention to provide an electric resistance sensor in a thin film shape. This sensor includes a thin line unit consisting of a plurality of thin lines. Film-like of lines enables one not only to accurately measure a low corrosion rate but to monitor localized corrosion behaviors such as pitting and crevice. The fabrication method of film-type sensor is described in this invention.

It is another object of the present invention to provide a method for precisely measuring a corrosion rate of facilities by using an electric resistance sensor in a thin film shape.

In order to achieve the above-described objects of the present invention, there is provided an electric resistance sensor for measuring a corrosion rate including: an insulating substrate having a predetermined size; a plurality of distributing units consisting of a conductive material and formed on the insulating substrate; a plurality of connecting units formed at each one end portion of the distributing units, electrically connecting the distributing units to an external circuit, and consisting of a conductive material; a thin line unit formed between the plurality of distributing units, and having a plurality of conductive thin lines electrically connected to the distributing lines; and a protecting layer formed on the substrate except for the thin line unit having a predetermined region in order to seal the distributing units and the connecting units.

BRIEF DESCRIPTION OF THE DRAWINGS

The present invention will become better understood with reference to the accompanying drawings which are given only by way of illustration and thus are not limitative of the present invention, wherein.

DETAILED DESCRIPTION OF THE INVENTION

A structure of an electric resistance sensor for measuring a corrosion rate (hereinafter, referred to as 'electric resistance sensor'), a fabrication method therefor, and a measurement method using the same in accordance with the present invention will now be described in detail with reference to the accompanying drawings.

Figure 1:
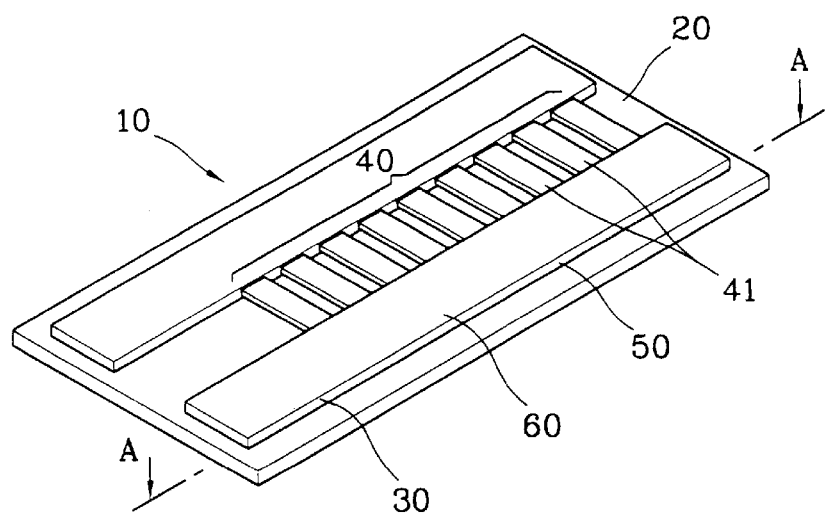
FIG. 1 is a perspective view illustrating an electric resistance sensor in accordance with the present invention.
Figure 2:
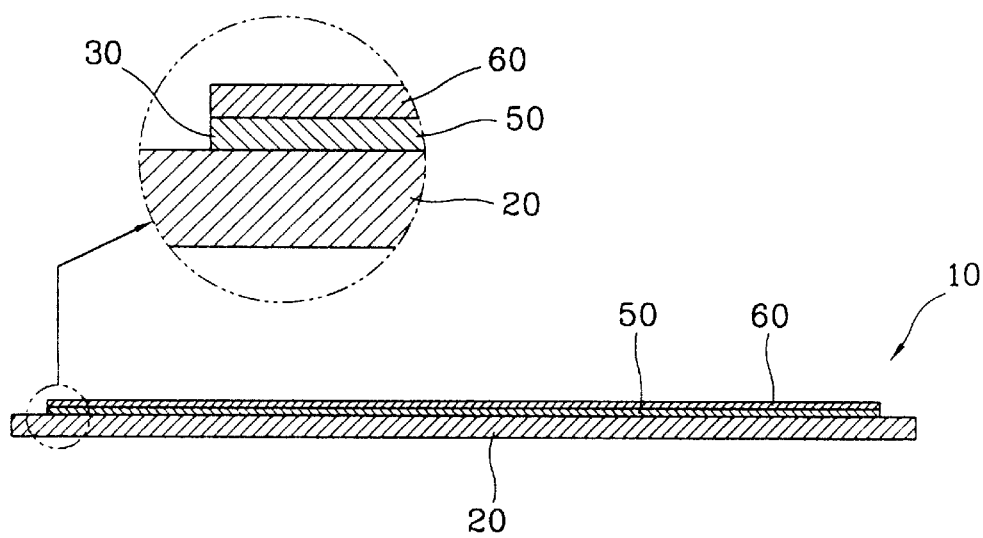
FIGS. 2 and 3 are cross-sectional views taken along line A-A' in FIG. 1.
Figure 3:
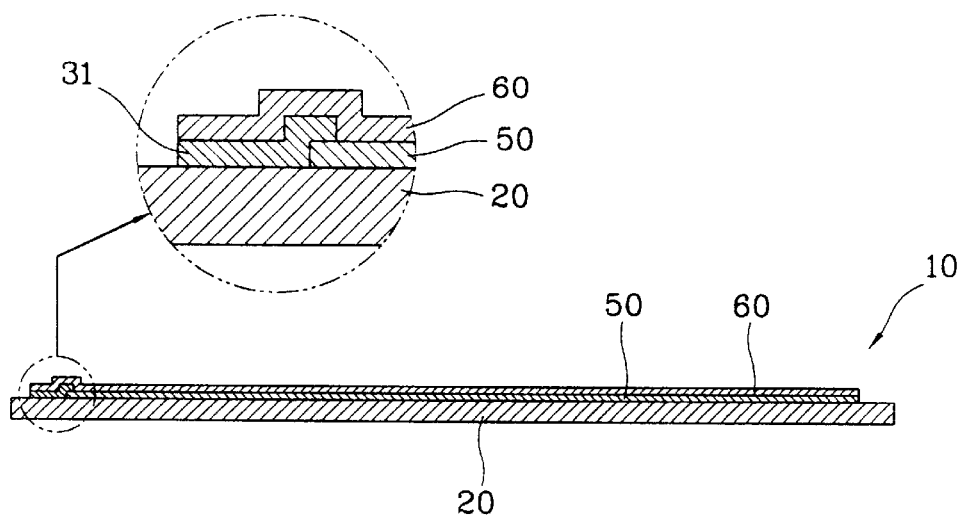

Firstly, the structure of the electric resistance sensor in accordance with the preferred embodiment of the present invention will now be explained with reference to FIGS. 1 to 3. FIG. 1 is a perspective view illustrating the electric resistance sensor in accordance with the preferred embodiment of the present invention. FIGS. 2 and 3 are cross-sectional views taken along line A-A'.

As shown therein, two distributing units 50 consisting of a conductive material, especially a metal thin film are formed on a flat substrate 20 consisting of an insulating material and having a predetermined size. A thin line unit 40 including a plurality of thin lines 41 having their both end portions connected to each distributing unit 50 is formed on the substrate 20 between the two distributing units 50. Advantageously, the thin line 41 consists of a conductive material, especially a metal thin film which is identical to a material of facilities where the corrosion rate is measured. When a thickness of the thin line is less than 10 nm, the thin line may be easily broken before it is exposed to a corrosion environment. In case a thickness of the thin line is greater than 20 $\mu$m, it is not susceptible to the corrosion environment. Accordingly, it is preferable that the metal thin film composing the thin line 41 has a thickness of 10 nm to 20 $\mu$m.

A connecting unit 30 electrically connecting the electric resistance sensor 10 to a unit (not shown) data processing the corrosion rate of the electric resistance sensor 10, such as a computer is formed at each one end portion of the distributing units 50. Referring to FIG. 2, the connecting unit 30 may be formed in a single body with the distributing unit 50. As depicted in FIG. 3, a connecting unit 30 consisting of a material having superior conductivity may be fixedly adhered to one end portion of the distributing unit 50. In addition, a protecting layer 60 consisting of an insulating and corrosion-resisting pigment, and sealing the distributing units 50 and the connecting units 30 is formed on the substrate 20 except for the thin line unit 40 having a predetermined region to be exposed to the corrosion environment.

A length from one connecting unit 30 to the other connecting unit 30 via the distributing units 50 and each thin line 41 may be formed identical so that each electric current route including thin line 41 have a same electric resistance.

Figure 4:
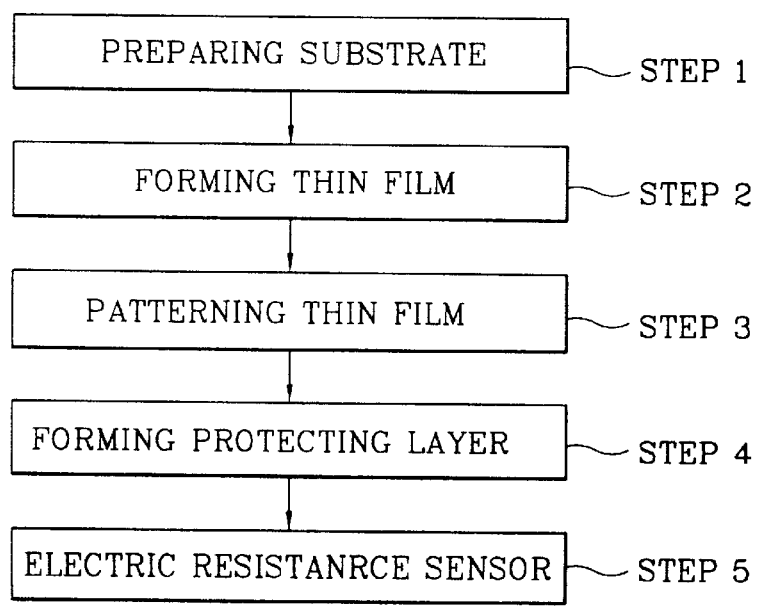
FIG. 4 is a block diagram illustrating sequential steps of a method for fabricating the electrical resistance sensor in accordance with the present invention.
Figure 5:
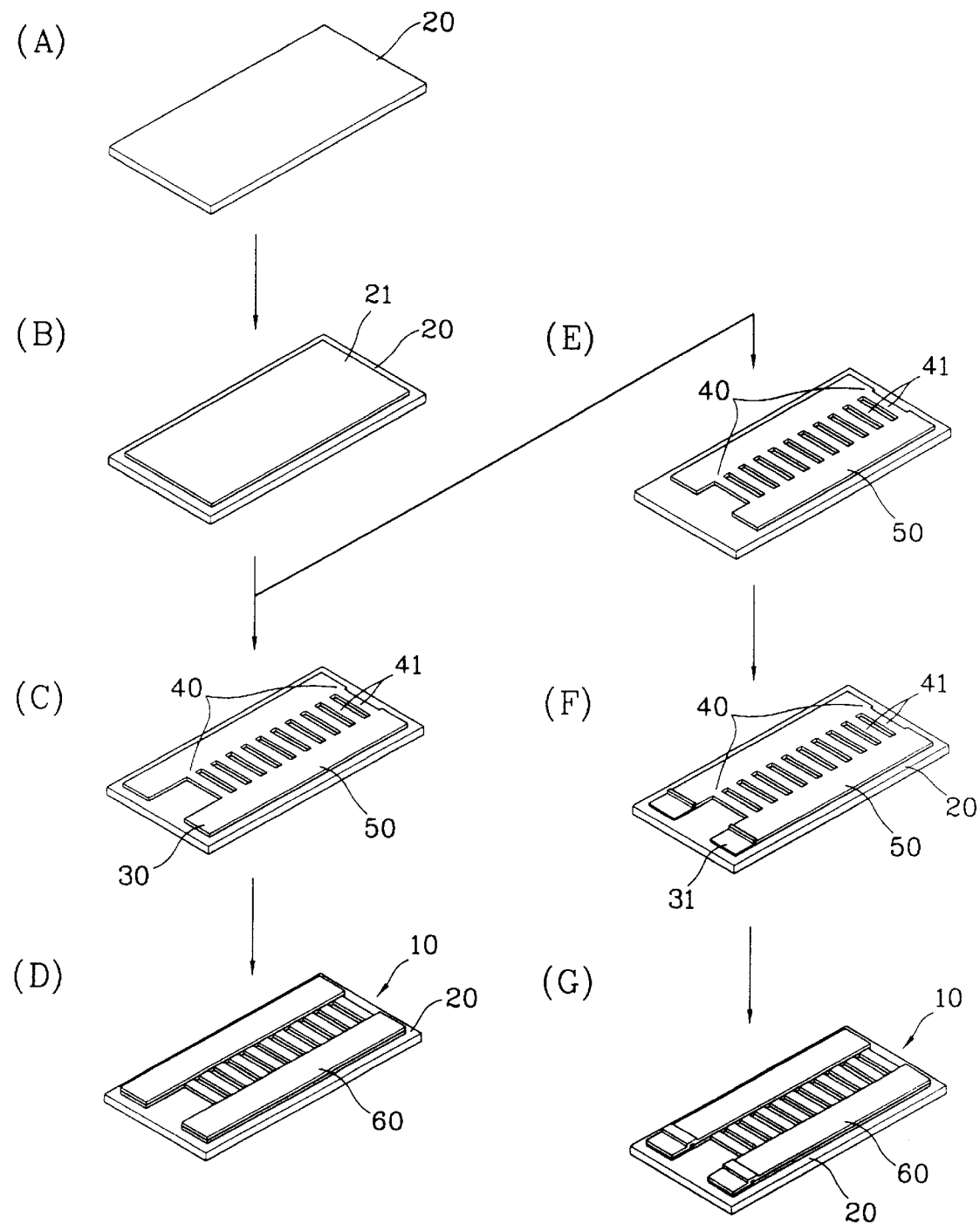
FIGS. 5a to 5g illustrate a preferred embodiment in accordance with the fabrication method of FIG. 4.

FIG. 4 is a block diagram illustrating sequential steps of the fabrication method for the electric resistance sensor in accordance with the preferred embodiment of the present invention. FIGS. 5a to 5g illustrate a concrete embodiment in accordance with the fabrication method of FIG. 4. Each step of the fabrication method as shown in FIG. 4 will now be described with reference to FIGS. 5a to 5g.

In a first step, the insulating layer 20 having a predetermined size on which a thin film can be formed is prepared. (FIG. 5(a)) In a second step, a conductive thin film, especially a metal thin film 21 is formed at a thickness of 10 nm to 20 μm on the insulating substrate 20 in accordance with one of thin film formation processes, such as a vacuum deposition process, a sputtering process and a plating process. It is advantageous that the metal thin film 21 consists of an identical material to a material of the facilities where the corrosion rate is measured. (FIG. 5(b)) Thereafter, in a third step, the metal thin film 21 is patterned in accordance with an etching process, especially a chemical etching process. The connecting units 30, the thin line unit 40 and the distributing units 50 may be formed together by the patterning (FIG. 5(c)). In addition, the thin line unit 40 and the distributing units 50 except for the connecting units 30 may be formed by the patterning (FIG. 5(e)). In the case that the connecting unit 30 is not formed by the etching process, a specific connecting unit 31 is fabricated with a material having superior conductivity, and closely adhered to one end portion of the distributing unit 50 (FIG. 5(f)). At last, in a fourth step, a conductive unit (not shown) such as a wire electrically connecting the electric resistance sensor to a unit (not shown) data processing the corrosion rate is closely adhered to the connecting units 30, 31. Then, the protecting layer 60 is formed on the substrate 20 except for the thin line unit 40 having a predetermined region to be exposed to the corrosion environment, by spreading and hardening a pigment having insulating and corrosion-resisting properties in order to seal the distributing units 50 and the connecting units 30, 31. (FIGS. 5(d) and 5(g)). Accordingly, fabrication of the electric resistance sensor in accordance with the preferred embodiment of the present invention is finished. In another example of the fourth step, the protecting layer 60 is formed on the substrate 20 except for the thin line unit 40 having a predetermined region to be exposed to the corrosion environment, by spreading and hardening the pigment having the insulating and corrosion-resisting properties in order to seal the whole distributing units 50 and partial regions of the connecting units 30, 31. Thereafter, the conductive unit (not shown) such as a wire is fixedly adhered to the exposed connecting units 30, 31. A specific protecting cap or layer is formed so as to seal the conductive unit (not shown) and the exposed connecting unit 30.

Figure 6:
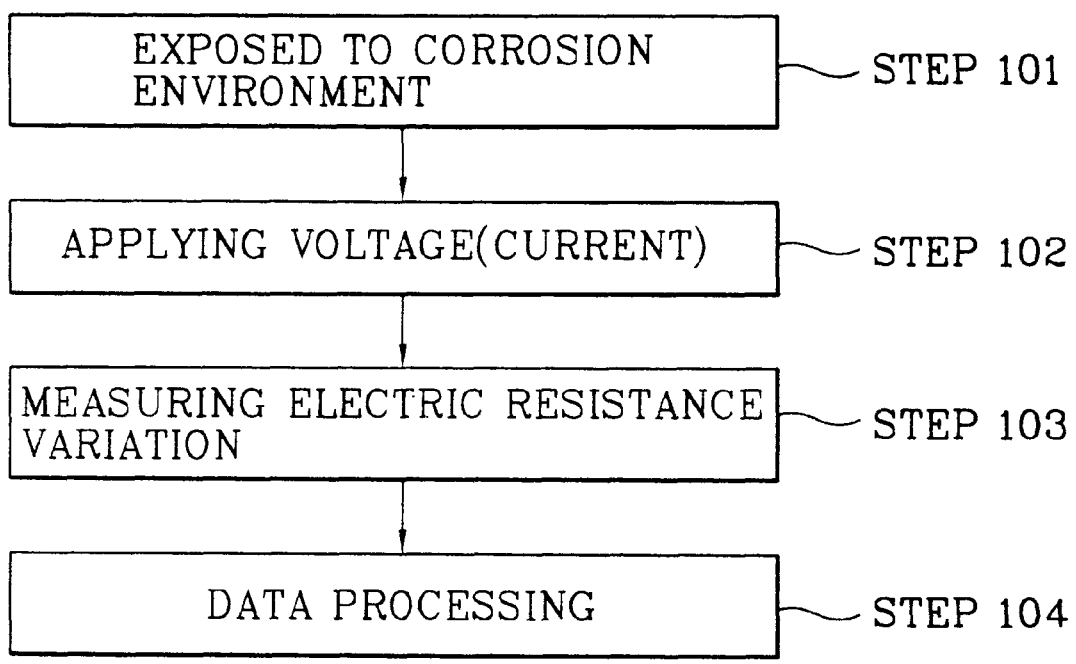
FIG. 6 is a block diagram illustrating sequential steps of a method for measuring a corrosion rate by using the electric resistance sensor in accordance with the present invention.

FIG. 6 illustrates the method for measuring the corrosion rate by employing the electric resistance sensor in accordance with the present invention.

The electric resistance sensor 10 is deposited or soaked in the corrosion environment, such as soil, sea water, fresh water, chemicals and atmosphere, and thus exposed to the corrosion environment. (Step 101) Here, the conductive unit such as the wire electrically connecting the electric resistance sensor 10 to the unit (not shown) data processing the corrosion rate of the electric resistance sensor 10, such as the computer is being connected to the connecting units of the electric resistance sensor 10. Thereafter, a predetermined voltage or current is applied to the connecting units of the electric resistance sensor 10. (Step 102) When the predetermined voltage or current is applied to the connecting units 30, 31, the current flows through the distributing units 50 connected to the connecting units 30, 31 and the thin line unit 40 consisting of a plurality of thin lines 41. Here, as each thin line 41 exposed to the corrosion environment is corroded, resistance values of the thin lines 41 are varied. As a result, a resistance value of the electric resistance sensor 10 is varied. Such a variation of the resistance value may be measured by the current variation when the predetermined voltage is applied to the connecting units 30, 31. To the contrary, in case the predetermined current is applied to the connecting units 30, 31, the variation of the resistance value can be measured by the voltage variation. (Step 103) At last, the 102nd step and the 103rd step are repeatedly carried out, thereby measuring and data processing the variation of the resistance value of the electric resistance sensor 10 in accordance with the time (Step 104).

Figure 7A:
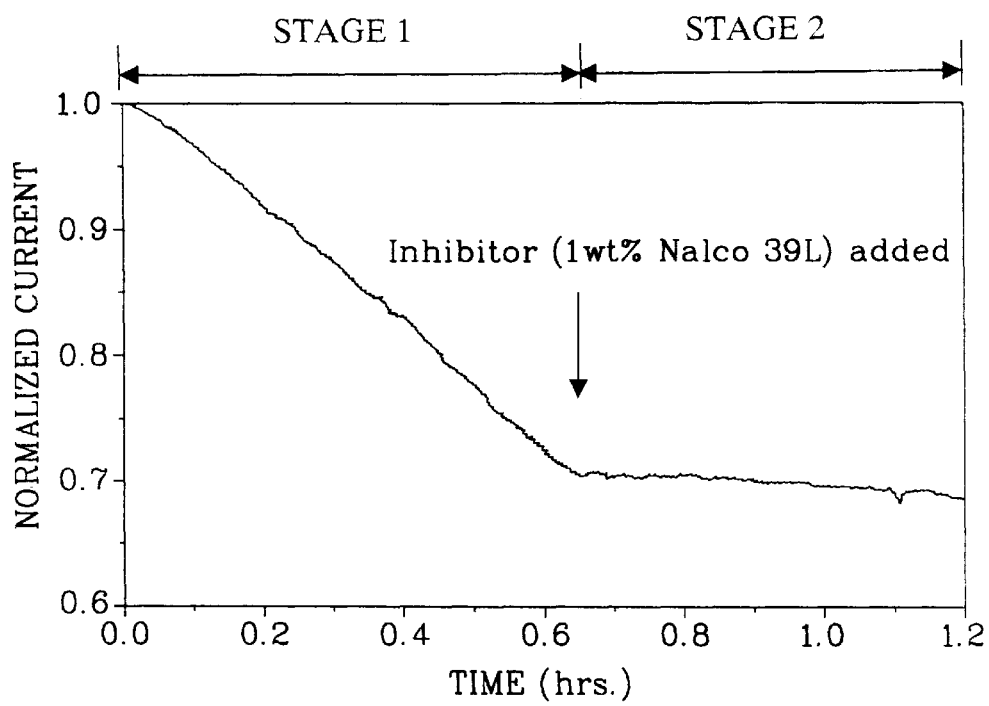
FIGS. 7a and 7b are graphs respectively illustrating a current variations in regard to a measurement time in accordance with the present invention.
Figure 7B:
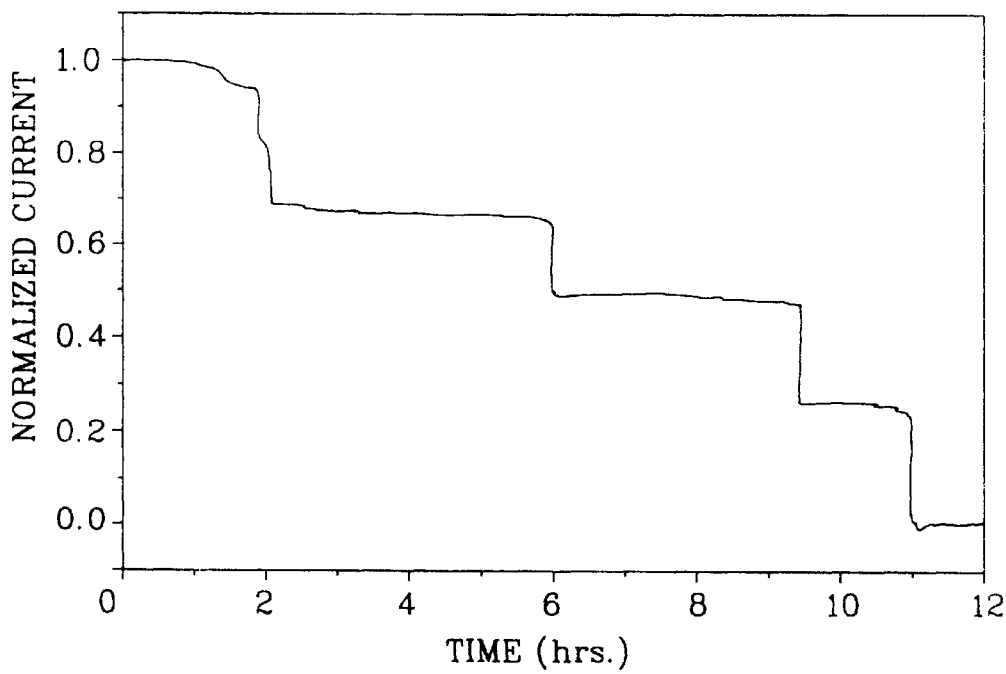

FIGS. 7a and 7b illustrate experiment results obtained by the measurement method for the corrosion rate by using the electric resistance sensor 10 in accordance with the present invention.

FIG. 7a illustrates current variations during the first step of soaking and corroding the electric resistance sensor 10 into 3% NaCl solution, applying the predetermined voltage to the electric resistance sensor 10, and during the second step of adding an inhibitor of 1 wt % Nalco39L to 3% NaCl solution.

The current is constantly reduced in accordance with the time in the first step because a regular corrosion that the conductive region of each thin line 41 composing the thin line unit 40 is regularly reduced takes place due to the progressing of the corrosion. That is to say, as the thin lines 41 are regularly corroded, the conductive region where the current can flow is decreased, and thus the resistance is increased. As a result, the current is reduced at a constant slope in accordance with the time.

In the case that the inhibitor of 1 wt % Nalco39L is added to 3% NaCl solution, the corrosion is restricted, and thus the corrosion rate of the thin lines 41 is remarkably decreased. Accordingly, a slope of the current decrease becomes closer to zero(0). Here, it is notable that the electric resistance sensor 10 sensitively reacts as soon as the inhibitor is added to NaCl solution. It is because the thin lines 41 to be corroded consist of a thin film, and thus a width of the resistance variations is large even in accordance with a slight difference of the corrosion environment.

FIG. 7b illustrates variations of the current passing through the electric resistance sensor 10 in accordance with the time by applying the predetermined voltage to the electric resistance sensor 10, and by soaking and corroding the electric resistance sensor 10 into 3% NaCl solution at a temperature of 55° C. added with the inhibitor of 1 wt % Nalco39L.

As shown therein, the current is fitfully varied. Here, all the thin lines 41 composing the thin line unit 40 exposed to the corrosion environment are not regularly corroded. That is, the resistance of the electric resistance sensor 10 is fitfully varied because the local corrosion that the thin lines 41 are locally corroded takes place. Consequently, the electric resistance. sensor in accordance with the present invention can be applied not only when the corrosion is entirely generated but also when the corrosion is generated in a pitting shape.

The electric resistance sensor for measuring the corrosion rate, and the measurement method using the same in accordance with the present invention can precisely sensitively measure the resistance variations of the electric resistance sensor resulting from the variations of the corrosion environment, and thus can be applied when stability to the corrosion is required and when the facilities are susceptible to the corrosion. In addition, the present invention can be applied not only when the corrosion is regularly generated but also when the corrosion in a pitting shape locally occurs.

The present invention may be mainly used for sensing a corrosion state of buried pipe lines and for sensing an inner corrosion state of a heat exchanger. In case the present invention is applied to the buried pipe lines, the sensor is electrically connected to the buried pipe lines, and a resistance variation is measured on the ground. When the present invention is applied to the heat exchanger, the sensor is provided to be soaked into an inner heat medium solution through a port installed at an outer surface of the heat exchanger, and a corrosion variation of a heat medium is measured.

As the present invention may be embodied in several forms without departing from the spirit or essential characteristics thereof, it should also be understood that the above-described embodiment is not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

What is claimed is:

1. An electric resistance sensor for measuring a corrosion rate, comprising:

an insulating substrate having a predetermined size;

two distributing units consisting of a conductive material and formed on the insulating substrate;

two connecting units formed at each one end portion of the distributing units, electrically connecting the distributing units to an external circuit, and consisting of a conductive material;

a thin line unit formed between the two distributing units, and having a plurality of conductive thin lines electrically connected to the distributing units; and a protecting layer formed on the substrate except for the thin line having a predetermined region, and sealing the distributing units, wherein the protecting layer consists of a pigment having at least one of an insulating property and a corrosion-resisting property.

2. The electric resistance sensor according to claim 1, wherein the distributing units, the thin line unit and the connecting units consist of a metal thin film, and are formed in a single body.

3. The electric resistance sensor according to claim 1, wherein the two distributing units are formed in parallel to one another.

4. The electric resistance sensor according to claim 1, wherein the thin lines composing the thin line unit are formed in parallel to one another.

5. The electric resistance sensor according to claim 1, wherein a length from one connecting unit to the other connecting unit via the distributing units and each thin line is formed identical.

6. The electric resistance sensor according to claim 2, wherein the connecting units are separately fabricated, and closely adhered to each one end portion of the distributing units.

7. The electric resistance sensor according to claim 2, wherein the metal thin film has a thickness of 10 nm to 20 $\mu$m.

8. An electric resistance sensor for measuring. a corrosion rate, comprising:

a thin line unit including a plurality of thin lines consisting of a conductive material;

a distributing unit for applying a predetermined voltage or current to the thin line unit; and a protecting layer for exposing merely the thin line unit at a predetermined region, wherein the protecting layer consists of a pigment having at least one of an insulating property and a corrosion-resisting property.

* * * * *